United States Patent [19]

Iwao et al.

[11] 4,183,917
[45] Jan. 15, 1980

[54] EMULSION-TYPE HAIR CONDITIONER COMPOSITION

[75] Inventors: Shuji Iwao, Tokyo; Tetsuya Abe, Yokohama; Tsutomu Yoshida, Narashino; Akemi Wada, Tokyo, all of Japan

[73] Assignee: The Lion Dentifrice Co., Ltd., Tokyo, Japan

[21] Appl. No.: 848,691

[22] Filed: Nov. 4, 1977

[30] Foreign Application Priority Data

Dec. 25, 1976 [JP] Japan .................................. 51-157202
Jun. 2, 1977 [JP] Japan .................................. 52-65150

[51] Int. Cl.² ............................................. A61K 7/06
[52] U.S. Cl. ...................................... 424/70; 252/316; 424/365
[58] Field of Search .................. 424/70, 365; 252/316

[56] References Cited

U.S. PATENT DOCUMENTS

| | | | |
|---|---|---|---|
| 3,061,519 | 10/1962 | Rosekrans | 424/70 |
| 3,101,300 | 8/1963 | Siegal et al. | 424/70 |
| 3,101,301 | 8/1963 | Siegal et al. | 424/70 |
| 3,102,114 | 8/1963 | Komori et al. | 424/70 X |
| 3,341,465 | 9/1967 | Kaufman et al. | 252/316 |
| 3,536,810 | 10/1970 | Moculeski | 424/70 X |
| 3,577,528 | 5/1971 | McDonough | 424/70 |
| 3,740,421 | 6/1973 | Schmolka | 424/70 X |
| 3,886,287 | 5/1975 | Kobayashi et al. | 424/70 X |
| 4,073,881 | 2/1978 | Imai et al. | 424/70 |

Primary Examiner—James O. Thomas, Jr.
Assistant Examiner—Vera C. Clarke
Attorney, Agent, or Firm—Ladas, Parry, Von Gehr, Goldsmith & Deschamps

[57] ABSTRACT

A hair conditioner composition in the form of an oil-in-water type emulsion comprising a high molecular synthetic oil with molecular weight of 1,500, selected from the group consisting of poly-alkyl glycol mono-alkyl ethers, phosphonates and high fatty acid esters thereof and alkylene oxide polyol adducts; a cationic surface active agent, a nonionic surface active agent and water. This composition may also include a liquid ester oil as optional component.

6 Claims, No Drawings

EMULSION-TYPE HAIR CONDITIONER COMPOSITION

BACKGROUND OF THE INVENTION

1. Field of the Invention

This invention relates to the hair conditioner compositions in the form of an oil-in-water type emulsion, such as hair rinse, hair cream and other preparations for hair treatment.

2. Description of the Prior Art

Heretofore, the hair conditioner compositions in the form of an oil-in-water type emulsion (hereinafter referred to as "o/w type emulsion") such as hair cream have been produced by emulsifying in water an oil-phase material having the molecular weight of around or less than 500 and a simple chemical structure, such as for example liquid paraffin, vaseline, (Trademark) higher alcohols, higher fatty acids, esters, lanolin derivatives or squalane, by using as emulsifier an anionic surface active agent, glyceryl monostearate or ester or ether type nonionic surface active agent. However, these known hair conditioner compositions, although capable of relatively simple and stabilized emulsification of the oil phase material, often prove unsatisfactory in use effect such as retention of smooth comb running, flexibility and hair fixability, or feel of use such as tackiness or performance. For instance, if liquid paraffin is used as a major raw material (major oil phase), the product has a sense of tackiness.

On the other hand, high molecular synthetic oils with molecular weights of over 1,500, such as for example polyoxypropylene monobutylether, are capable of producing an excellent hair fixing effect, so that they are widely used as major material for hair fixing preparations. However, these synthetic oil materials are higher in molecular weight, complicated in chemical structure as compared with liquid paraffin or the like, and also fairly high in polarity in comparison with mineral oils such as liquid paraffin, so that they are very hard to emulsify and also extremely unstable even if emulsified. Therefore, use of said synthetic oils in the form of an emulsion has been attended by great difficulties. In case of preparing an o/w type emulsion by using one of said synthetic high-molecular oils, even if emulsification is accomplished according to a known method by using a commonly employed type of surface active agent (such as fatty acid soap, or glyceryl monostearate,), the state of emulsion and stability with aging become worse by increasing the synthetic oils, and also the texture and luster of the cream (emulsion) become extremely worse. Therefore, the above-said synthetic oils are mostly used not as emulsion type hair fixing preparations but as liquid type preparations, but such high molecular liquid synthetic oil materials involve the problem in the feeling of use since such materials have inherent tackiness and give a sense of greasiness. Therefore, development of a hair conditioner composition capable of eliminating such poor feeling of use and also having excellent long-term hair fixing and conditioning effects has been strongly required.

SUMMARY OF THE PRESENT INVENTION

An object of this invention is to provide a hair conditioner composition capable of producing a better emulsion and also excellent stability.

Another object of this invention is to provide a hair conditioner composition having fine texture, excellent luster and good adhesiveness onto the hair and free from stickiness and unfavorable shining.

A further object of this invention is to provide a hair conditioner composition having high retention of smooth comb running property, flexibility and hair fixability as well as good feeling of use.

Other objects, features and advantages of the present invention will be apparent from the following detailed description of the invention.

According to the present invention, there is provided a hair conditioner composition comprising 1 to 50% by weight of a high molecular synthetic oil with molecular weight of over 1,500, selected from the group consisting of polyalkylene glycol monoalkyl ethers, phosphates and higher fatty acid esters thereof and alkylene oxide-polyol adducts, 0.05 to 5% by weight of a cationic surface active agent, 0.5 to 10% by weight of a nonionic surface active agent and water. This composition may contain a liquid ester oil well compatible with said cationic surface active agent as optional component.

DESCRIPTION OF THE PRESENT INVENTION

The "high molecular synthetic oil" used in this invention is a material having molecular weight of over 1,500 and staying in a liquid state, and the examples of such material are polyalkyleneglycol monoalkyl ethers expressed by the following general formula:

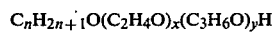

(where $n \geq 2$, $0 \leq x$ and $30 \leq y$, preferably $4 \leq n \leq 18$, $3 \leq x \leq 15$, and $50 \leq y \leq 80$, (polyalkyleneglycol monoalkylether), polyalkyleneglycol alkylesters, polyol ethers of polyalkylene glycol obtained by adding an ethylene oxide and/or a propylene oxide to a polyol, and the derivatives thereof such as phosphate, higher fatty acid esters and polymers of $\alpha$-olefin. Such synthetic oil material is used for giving a sense of moisture effect and improving retention of excellent hair fixing and conditioning effects while bettering the feeling of use. Such synthetic oil is usually blended in an amount of 1 to 50 weight%, preferably 5 to 30 weight%.

For emulsifying said synthetic oil in water, a cationic surface active agent and a nonionic surface active agent are used in combination as emulsifiers. The cationic surface active agent used for this purpose may be for example a quaternary ammonium salt having an alkyl group with 10 to 22 carbon atoms, such as for example dialkyldimethylammonium salt, alkyltrimethylammonium salt, alkyldimethylbenzylammonium salt or alkylimidazolium salt, but most preferred for use in this invention is a dialkyldimethylammonium salt having an alkyl group with more than 16 carbon atoms. The addition of such cationic surface active agent in the emulsion composition should be within the range of 0.05 to 5 weight%, preferably 0.5 to 3 weight%. If this addition is less than the above-said range, stable emulsion of said synthetic oil may not be accomplished.

The nonionic surface active agent used in this invention may be a polyoxyethylenic material such as polyoxyethylene alkylether or a polyoxyethylene-polyoxypropylene copolymer, but most preferred is an ether type nonionic surface active agent having an alkyl group with 12 to 18 carbon atoms, such as for example polyoxyethylene stearylether or polyoxyethylene hydrogenated castor oil. Such ether type nonionic surface active agents are preferably prepared by mixing a polyoxyethylene alkylether with the hydrophilic-lipophilic balance (hereinafter referred to as HLB) of 7 to 10 and a polyoxyethylene alkylether with HLB of 13 to 16 in the weight ratio of 5:1 to 1:5, preferably about 2:1, and such ether type nonionic surface active agent is blended in the composition in an amount of 0.5 to 10 weight%, preferably 0.5 to 2 weight%.

It is desirable that the blend ratio of said cationic surface active agent to ether type nonionic surface active agent is 1:5 to 5:1 preferably 1:2 to 2:1 (by weight ratio), and such blending can further assure stable emulsification of the synthetic oil in water to improve the feeling of use.

In the composition of this invention, it is possible to blend as optional component a liquid ester oil having good compatibility with said cationic surface active agent. Addition of such ester can further improve the use effect (such as retention of conditioning effect or hair fixing effect) as well as the feeling of use of the hair conditioner composition. Such liquid ester oil used in this invention is of the type having an alkyl group with more than 6 carbon atoms and slightly polar. The ester oil materials having the inorganic-organic balance (IOB) of less than 0.5, particularly less than 0.2, have good compatibility with the cationic surface active agent as shown in Table 1 below.

Table 1

|  | IOB | Compatibility with cationic surface active agent | Remarks |
| --- | --- | --- | --- |
| Isopropyl isostearate | 0.15 | A |  |
| Isopropyl laurate | 0.21 | B-C |  |
| Isopropyl myristate | 0.18 | B |  |
| Isopropyl palmitate | 0.16 | B |  |
| Hexyl laurate | 0.17 | B | Usable |
| Oleyl oleate | 0.09 | A |  |
| Cetyl isooctanate | 0.13 | B |  |
| Isostearyl palmitate | 0.09 | A |  |
| Diisopropyl adipate | 0.55 | D |  |
| Diethyl phthalate | 0.56 | D | Unusable |
| Ethyl acetate | 0.75 | D |  |

A:excellent
B:good
C:slightly bad
D:bad;

The addition of said liquid ester oil should be within the range of 0.1 to 10 weight% as the addition within this range can improve retention of use effect such as hair fixing and conditioning effect as well as feeling of use such as limited tackiness and good performance. The addition over the above-said range results in the increased sense of tackiness and poor feeling of use. The most preferred range of loading of the liquid ester oil is from 1 to 5 weight%.

In addition to the above-said synthetic oil, cationic surface active agent, nonionic surface active agent, liquid ester oil and water, it is also possible to blend other additives such as a vegetable oil (linseed oil, castor oil, olive oil,), a mineral oil (e.g. liquid paraffin, Vaseline:;; paraffin wax,), a hydrocarbon (e.g. squalane,), lanolin, a higher alcohol, a higher fatty acid, a silicone (e.g. dimethylpolysiloxane, methylphenylpolysiloxane,), an antioxidant; a perservative, an active principle (aminoacid derivatives, polypeptides, vitamin derivatives,), a polyol, a dye, a perfume, a surfactant (amphoteric, nonionic or other types of surface active agent), a resin (anionic, cationic or amphoteric resin) with these additives being suitably selected depending on the type of the hair conditioner composition to be produced.

For preparing a hair conditioner composition in the form of an o/w type emulsion, such as for example hair rinse, hair cream or hair treatment preparations, from the blend of said synthetic oil, cationic and nonionic surface active agents, water, liquid ester oil as optional component and other additives, first the water-soluble components are dissolved in water while mixing the oil-soluble components with each other according to a known method, and after adding the oil phase to the water phase, said both phases being heated if necessary, the mixture is agitated and emulsified by a mixer.

The thus obtained hair conditioner composition can be used in the same way as the conventional hair conditioner compositions of this type. For instance, in the case of hair rinse, a suitable quantity of such rinse is directly applied to the shampooed hair or scalp and, after sufficient rubbing or massage, it is washed away.

As described above, in preparation of an o/w type emulsion composition of this invention by emulsifying a high molecular synthetic oil with molecular weight of over 1,500 in water, such synthetic oil can be easily and surely emulsified by combined use of a cationic surface active agent and a nonionic surface active agent as emulsifier, and the obtained o/w type emulsion composition has very excellent stability and there takes place no creaming or separation even if the composition is kept under a high temperature of around 45° C., let alone room temperature. Also, the emulsion composition according to this invention is excellent in keeping quality, texture, luster, spreadability and touch and has good appearance and use characteristics as well as very excellent affinity to skin and sorption onto hair. Although the synthetic oil itself has tackiness and gives a sense of oiliness, the emulsified product has almost no such tackiness, and the emulsion compositions (cream, lotion, etc.) of this synthetic oil have less tackiness and oil greasiness than the cream, lotion, etc., using liquid paraffin as oil phase material. Thus, the composition of this invention has solved the problem of tackiness, greasiness and other defects inherent to the conventional liquid hair fixing or treating preparations. Further, the o/w type emulsion composition according to this invention is capable of producing a wide variety of preparations ranging from cream to lotion with various viscosities by suitably varying the addition of the synthetic oil, and the obtained products possess various excellent properties. Thus, the composition of this invention finds best application for preparation of emulsion type cosmetics.

Also, blending of a liquid ester oil with good compatibility with said cationic surface active agent allows proper supply of oil to the hair or scalp which has been degreased by shampooing, and gives gloss and pliance to the hair while bettering sorption and affinity of the composition to the hair and scalp, thus improving retention of smooth comb running and the conditioning and hair fixing effect. For example, if this hair conditioner is used for men's hair, the hair can be fixed with no need of using any hair liquid and also the hair does not tangle while sleeping. Further, the hair conditioner composition according to this invention has good spreadability, gives no sense of tackiness in use, and is capable of providing excellent finish. Still further, the composition of this invention can be rendered into a good emulsion to provide a product with excellent texture, luster and touch. It also has good storage stability; there takes place no separation or other undesirable phenomenon even if the composition is kept under a high temperature of around 45° C., let alone room temperature, for a period of about 1 month.

The following examples are given as specific illustrations of the present invention. It should be understood, however, that the present invention is not limited to the specific details set forth in the examples.

EXPERIMENTAL EXAMPLE

Both water and oil phases having the compositions shown in Table 2 were heated to 80° C. and then the oil phase was added into the water phase, and the mixture was agitated and emulsified by a mixer for 5 minutes, followed by cooling. There were thereby prepared various emulsion compositions (Specimen Nos. 1 to 14), and their storage stability and feeling of use (spread sand tackiness) were examined. The results are shown in the same table.

The storage stability was determined by observing the condition after one-month storage of each specimen at 45° C. and one-month storage at temperatures varying between 20° and 40° C., and such storage stability was rated according to the following standards:

A: excellent
B: good
C: slightly bad
D: bad

The storage stability test was made by packing each prepared emulsion composition in a glass bottle or plastic tube and keeping three pieces of specimens for one month at 45° C. keeping them for 1 month at 20° C. and 40° C. on alternate days, and the stability was observed with the naked eye and compared with the corresponding composition preserved at room temperature. Preserved at 45° C. for one month:

◎: No change as compared with the control (composition preserved at room temperature). Excellent texture and gloss maintained.

O: Substantially no change as compared with the control, but gloss was slightly worsened.

Δ: Both texture and gloss were worse than the control. Workability was also bad.
X: Separation took place.

Preserved at 20°–40° C. cycle for one month:

◎: No change as compared with the control. Both texture/and gloss were fine.
O: Slightly worse in texture than the control.
Δ: Both texture and gloss were worse than the control.
X: Separation occured.

(The same condition was used in both glass bottle and plastic tube).

As for feeling of use (spread and tackiness), a blind organoleptic examination was conducted on spreadability and tackiness by using a 20-person panel.

|  |  | Excellent | Good | Bad | Very bad |
|---|---|---|---|---|---|
| (1) Spread | Emulsions of this invention | 17 | 3 | 0 | 0 |
|  | Conventional products | 0 | 5 | 2 | 13 |

|  |  | Absolutely no tackiness | Substantially no tackiness | Slightly tacky | Considerably tacky |
|---|---|---|---|---|---|
| (2) Tackiness | Emulsions of this invention | 15 | 5 | 0 | 0 |
|  | Conventional products | 0 | 8 | 5 | 7 |

|  | Tackiness | Spread |
|---|---|---|
| A: | Absolutely no tackiness | Excellent |
| B: | Substantially no tackiness | Good |
| C: | Slightly tacky | Slightly bad |
| D: | Considerably tacky | Very bad |

Table 2

|  |  | Example (Specimen No.) |  |  |  |  | Comparative example (Specimen No.) |  |  |  |  |  |  |  |  |
|---|---|---|---|---|---|---|---|---|---|---|---|---|---|---|---|
|  |  | 1 | 2 | 3 | 4 | 5 | 6 | 7 | 8 | 9 | 10 | 11 | 12 | 13 | 14 |
| Components | POP monobutylether (M.W. 4000) | 20 | 10 | 10 | — | — | — | 20 | — | — | — | — | 20 | — | 10 |
|  | Triol (M.W. 3600) | — | 10 | — | 10 | — | — | — | — | — | — | — | — | — | — |
|  | POP POE stearyl ether (m.W. 4000) | — | — | — | — | 20 | 10 | — | — | — | 5 | — | — | 10 | — |
|  | Fluid paraffin | — | — | — | 10 | — | 10 | — | 20 | 20 | 15 | — | — | 10 | 10 |
|  | Castor oil | — | — | 10 | — | — | — | — | — | — | — | 20 | — | — | — |
|  | Stearic acid | 2 | 2 | 2 | 2 | 2 | 1 | 2 | 2 | 2 | 2 | 2 | 2 | 1 | 2 |
|  | Cetyl alcohol | 3 | 3 | 3 | 3 | 3 | 4 | 3 | 3 | 3 | 3 | 3 | 3 | 4 | 3 |
|  | POE/POP copolymer (M.W. 5000) | 0.5 | — | — | — | — | — | 0.5 | 0.5 | 0.5 | 0.5 | 0.5 | 0.5 | — | — |
|  | POE hardened castor oil (40 EO) | 0.1 | 0.1 | 0.1 | — | 0.1 | — | 0.1 | 0.1 | 0.1 | 0.1 | 0.1 | 0.1 | — | — |
|  | POE fatty acid ester (10 EO) | — | — | — | — | — | 1 | 1 | — | 1 | 1 | — | 1 | 1 | — |
|  | Sucrose ester | — | — | — | — | — | 1 | — | — | — | 1 | — | — | — | — |
|  | POE sucrose fatty acid ester (10 EO) | — | — | — | — | — | 2 | 2 | — | 2 | 2 | — | 2 | 2 | — |
|  | Triethanolamine soap | — | — | — | — | — | — | — | 3 | — | 3 | — | — | — | — |
|  | Distearyldimethylammonium chloride | 1 | 2 | 1 | 1 | 1 | — | — | 1 | — | — | 1 | — | — | — |
|  | Propylene glycol | 5 | 5 | 5 | 5 | 5 | 5 | 5 | 5 | 5 | 5 | 5 | 5 | 5 | 5 |
|  | Water | 67.2 | 66.7 | 67.7 | 67.8 | 67.7 | 66 | 63.4 | 67.2 | 63.4 | 65.4 | 67.2 | 66.4 | 67 | 67 |
|  | POE cetyl ether (HLB 7-10) | 0.8 | 0.8 | 0.8 | 0.8 | 0.8 | — | — | 0.8 | — | — | 0.8 | — | — | 2 |
|  | POE stearyl ether (HLB 13-16) | 0.4 | 0.4 | 0.4 | 0.4 | 0.4 | — | — | 0.4 | — | — | 0.4 | — | — | 1 |
| Effect | Storage stability kept at 45° C. for 1 month | A | B | A | A | A | D | D | A | B | D | B | D | D | D |
|  | Spread kept at 20°–40° C. | A | B | A | A | A | C | C | C | C | C | B | D | D | D |
|  | Tackiness for 1 month | A | B | A | A | A | C | B | D | D | C | B | — | — | — |
|  |  | B | B | B | B | A | A | C | D | D | B | D | — | — | — |

(Notes)
POP is abbreviation for polyoxypropylene, POE for polyoxyethylene, and M.W. for molecular weight. "40 EO" indicates "adduct with 40 moles of ethylene oxide". The numerical values for the respective components are all by weight %. Triol was prepared by adding propylene oxide to glycerin.

As apparent from the results shown in Table 2, use of a cationic surface active agent (dialkyldimethylammonium chloride) and a nonionic surface active agent, particularly polyoxyethylene alkylethers (polyoxyethylene cetyl ether and polyoxyethylene stearyl ether) as emulsifier allows stabilized emulsification of the synthetic oil in water, and also the obtained emulsion compositions are all excellent in feeling of use such as spreadability and tackiness.

On the other hand, if no cationic surface active agent is used, or if a combination of nonionic surface active agents themselves or a combination of a nonionic surface active agent and an anionic surface active agent is used as emulsifier to emulsify said synthetic oil, any of the resultantly obtained emulsion compositions is poor in stability and separation takes place easily when such compositions are kept at 45° C.

EXAMPLE I

Milky Hair Lotion

A milky hair lotion of the following composition was prepared according to the same procedure as described above.

| | |
|---|---|
| Polyoxyethylene polyoxypropylene monostearyl ether (M.W. 4000) | 20 wt % |
| Cetyl alcohol | 2 wt % |
| Distearyldimethylammonium chloride | 1 wt % |
| Sorbitol | 10 wt % |
| Polyoxyethylene nonylphenyl ether (with 10 moles of ethylene oxide) | 1 wt % |
| Polyoxyethylene nonylphenyl ether (with 3 moles of ethylene oxide) | 2 wt % |
| Methylparaben | 0.2 wt % |
| Propylparaben | 0.5 wt % |
| Liquid lanolin | 3 wt % |
| Water | 60.75 wt % |
| | 100 wt % |

EXAMPLE II

Hair Rinse

A hair rinse of the following composition was prepared in the similar way.

| | |
|---|---|
| Polyoxypropylene monobutyl ether (with 70 moles of propylene oxide) | 10 wt % |
| Cetyl alcohol | 2 wt % |
| Distearyldimethylammonium chloride | 2 wt % |
| Propylene glycol | 5 wt % |
| Polyoxyethylene lauryl ether (with 15 moles of ethylene oxide) | 0.5 wt % |
| Polyoxyethylene lauryl ether (with 8 moles of ethylene oxide) | 1 wt % |
| Water | 79.5 wt % |
| | 100 wt % |

EXAMPLE III

Cream Hair Conditioner

A cream hair conditioner having the following composition was prepared in the similar way.

| | |
|---|---|
| Triol (prepared by adding 70 to 100 moles of propylene oxide to glycerin) | 15 wt % |
| Liquid paraffin | 5 wt % |
| Stearic acid | 3 wt % |
| Cetyl alcohol | 2 wt % |
| Stearyltrimethylammonium chloride | 1 wt % |
| Polyoxyethylene hardened castor oil (with 40 moles of ethylene oxide) | 0.1 wt % |
| Polyoxyethylene lauryl ether (with 20 moles of ethylene oxide) | 0.5 wt % |
| Polyoxyethylene stearyl ether (with 6 moles of ethylene oxide) | 1 wt % |
| Propylene glycol | 5 wt % |
| Water | 67.4 wt % |
| | 100 wt % |

The emulsion compositions obtained in Examples I to III were all excellent in stability and had good feeling of use.

EXAMPLE IV

Hair rinses in the form of o/w type emulsions having the compositions (Specimen Nos. 15 to 20) shown in Table 3 were produced according to a normal method, and the conditioning effect, hair fixing effect and feeling of use of the products were evaluated. The results are also shown in Table 3.

The use effect and feeling of use were evaluated by an organoleptic test and expressed by using the following denotations.

Comb Running

A: There was no sense of resistance and comb running was smooth even after 24 hours.

B: There was no sense of resistance and comb running was smooth even after 12 hours.

C: There was no sense of resistance and comb running was smooth even after 2 to 3 hours.

D: There was noted a sense of resistance and comb running became awkward after 2 to 3 hours.

Flexibility

A: Soft touch and good flexibility were maintained even after 24 hours.

B: Soft touch and good flexibility were maintained even after 12 hours.

C: Soft touch and good flexibility were maintained even after 2 to 3 hours.

D: There was produced a sense of looseness and flexibility was worsened after 2 to 3 hours.

Hair Fixability

A: Hair set was maintained unchanged even after 48 hours.

B: Hair set was maintained unchanged even after 24 hours.

C: Hair set was maintained unchanged even after 12 hours.

D: Hair set gave way after 12 hours.

Tackiness

A: Absolutely no sense of tackiness was noted during use and after 24 hours.

B: Substantially no sense of tackiness was noted during use and after 24 hours.

C: A slight sense of tackiness was noted during use and after 24 hours.

D: Tackiness was noted during use and after 24 hours.

Performance (End effect) (after 2- to 3-hour natural drying)

A: Light and soft feeling.
B: Light feeling.
C: Slightly heavy feeling.
D: Heavy and clammy feeling.

Table 3

| Components | Specimen No. | Example 15 | 16 | 17 | 18 | Comparative Example 19 | 20 | 21 | 22 | 23 |
|---|---|---|---|---|---|---|---|---|---|---|
| POP monobutylether (100 PO) | | | | | 2 | | | | | 2 |
| POP/POE cetyl ether (m.W. 3600) | | | | 3 | | | | | 3 | |
| Triol (M.W. 4000) | | 1 | 3 | | 3 | | | 3 | | 3 |
| Liquid paraffin | | 2 | | 2 | | 5 | 2 | | 2 | |
| α-olefin polymer | | 2 | | | | | 3 | | | |
| Castor oil | | | 2 | | | | | 2 | | |
| Oleyl oleate | | | 1 | | 1 | | | | | |
| Cetyl isooctanate | | | | 1 | | | | | | |
| Isostearyl palmitate | | 1 | | | | | 1 | | | |
| Diisopropyl adipate | | | | | | 1 | | | 1 | |
| Diethyl phthalate | | | | | | | | | | 1 |
| POE lauryl ether (HLB 13-16) | | 1 | 1 | 1 | 1 | 1 | 1 | 1 | 1 | 1 |
| POE cetyl ether (HLB 7-10) | | 2 | 2 | 2 | 2 | 2 | 2 | 2 | 2 | 2 |
| Distearyldimethylammonium chloride | | 2 | 2 | | | 2 | 2 | 2 | | |
| Stearyldimethylbenzylammonium chloride | | | | 2 | 2 | | | | 2 | 2 |
| Cetyl alcohol | | 3 | 3 | 3 | 3 | 3 | 3 | 3 | 3 | 3 |
| Propylene glycol | | 5 | 5 | 5 | 5 | 5 | 5 | 5 | 5 | 5 |
| Water | | 81 | 81 | 81 | 81 | 81 | 81 | 82 | 81 | 81 |
| | Total | 100 | 100 | 100 | 100 | 100 | 100 | 100 | 100 | 100 |
| Use effect | Comb running | A | A | A | A | D | D | B | B | B |
| | Flexibility | B | A | B | A | D | D | C | C | C |
| | Hair fixability | A | A | B | A | D | D | C | C | C |
| Feeling of use | Tackiness | A | B | B | B | D | C | B | B | B |
| | Finish | B | A | B | A | D | C | B | B | B |

(Notes)
POP is abbreviation for polyoxypropylene, POE for polyoxyethylene, and M.W. for molecular weight, "100 PO" indicates "adduct with 100 moles of propylene oxide". The numerical values for the respective components are all by weight %. Triol was prepared by adding propylene oxide to glycerin.

EXAMPLE IV

Hair conditioning creams in the form of o/w type emulsions having the compositions (Specimen Nos. 21 to 26) shown in Table 4 were produced according to a normal method, and their use effect and feeling of use were evaluated after the manner of Example IV. The results are shown in Table 4. The figures and symbols have the same meanings as those of Table 3.

EXAMPLE VI

Hair treatment preparations in the form of o/w type emulsions having the compositions (Specimen Nos. 27 to 32) shown in Table 5 were produced according to a normal method, and their use effect and feeling of use were evaluated in the same way as Example 3. The results are also shown in Table 5. The figures and symbols of Table 5 have the same meanings as those of Table 3.

EXAMPLE 6

Hair treatment preparations in the form of o/w type emulsions having the compositions (Specimen Nos. 33 to 35) shown in Table 6 were produced according to a normal method, and their use effect and feeling of use were evaluated after the fashion of Example 3, with the results being also shown in Table 6. The figures and symbols of Table 6 have the same meanings as those of Table 3

Table 4

| Components | Example (Specimen No.) 21 | 22 | 23 | 24 | Comparative example (Specimen No.) 25 | 26 |
|---|---|---|---|---|---|---|
| POP monobutyl ether (100 PO) | 10 | | | 10 | | |
| POP/POE cetyl ether (M.W. 3600) | | | 20 | | | |
| Triol (M.W. 4000) | | 20 | | 20 | | |
| Liquid paraffin | 10 | | 10 | | 30 | 10 |
| α-olefin polymer | 10 | | | | | 20 |
| Castor oil | | 10 | | | | |
| Oleyl oleate | | 2 | | 2 | | |
| Cetyl isooctanate | | | 2 | | | |
| Isostearyl palmitate | 2 | | | | | 2 |
| Diisopropyl adipate | | | | | 2 | |
| Diethyl phthalate | | | | | | |
| POE lauryl ether (HLB 13-16) | 0.4 | 0.4 | 0.4 | 0.4 | 0.4 | 0.4 |
| POE cetyl ether (HLB 7-10) | 0.8 | 0.8 | 0.8 | 0.8 | 0.8 | 0.8 |
| Distearyldimethylammonium chloride | 1 | 1 | | | 1 | 1 |
| Stearyldimethylbenzylammonium chloride | | | 1 | 1 | | |
| Stearic acid | 2 | 2 | 2 | 2 | 2 | 2 |
| Cetyl alcohol | 5 | 5 | 5 | 5 | 5 | 5 |
| Lanolin | 1 | 1 | 1 | 1 | 1 | 1 |
| Propylene glycol | 5 | 5 | 5 | 5 | 5 | 5 |
| Water | 52.8 | 52.8 | 52.8 | 52.8 | 52.8 | 52.8 |
| Total | 100 | 100 | 100 | 100 | 100 | 100 |
| Use Comb running | A | A | A | A | D | C |

Table 4-continued

| Components | | Example (Specimen No.) | | | | Comparative example (Specimen No.) | |
|---|---|---|---|---|---|---|---|
| | | 21 | 22 | 23 | 24 | 25 | 26 |
| effect | Flexibility | B | A | B | A | D | C |
| | hair fixability | A | A | B | A | D | D |
| Feeling | Tackiness | A | A | B | A | D | D |
| of use | Finish | A | A | B | A | D | D |

Table 5

| Components | | Example (Specimen No.) | | | | Comparative example | |
|---|---|---|---|---|---|---|---|
| | | 27 | 28 | 29 | 30 | 31 | 32 |
| POP monobutyl ether (100 PO) | | | | | 10 | | |
| POP/POE cetyl ether (M.W. 3600) | | 10 | | 10 | | | |
| Triol (M.W. 4000) | | | 10 | | 10 | | |
| Liquid paraffin | | | | 10 | | 20 | 10 |
| α-olefin polymer | | 10 | | | | | 10 |
| Castor oil | | | 10 | | | | |
| Silicone oil | | 0.5 | 0.5 | 0.5 | 0.5 | 0.5 | 0.5 |
| Oleyl oleate | | | 3 | | 3 | | |
| Cetyl isooctanate | | | | 3 | | | |
| Isostearyl palmitate | | 3 | | | | | 3 |
| Diisopropyl adipate | | | | | | 3 | |
| Diethyl phthalate | | | | | | | |
| POE lauryl ether (HLB 13-16) | | 0.5 | 0.5 | 0.5 | 0.5 | 0.5 | |
| POE cetyl ether (HLB 7-10) | | 1 | 1 | 1 | 1 | 1 | 1 |
| Distearyldimethylammonium chloride | | 1 | 1 | 1 | 1 | 1 | 1 |
| Stearic acid | | 2 | 2 | 2 | 2 | 2 | 2 |
| Cetyl alcohol | | 4 | 4 | 4 | 4 | 4 | 4 |
| Lanolin | | 3 | 3 | 3 | 3 | 3 | 3 |
| Propylene glycol | | 5 | 5 | 5 | 5 | 5 | 5 |
| Water | | 60 | 60 | 60 | 60 | 60 | 60 |
| | Total | 100 | 100 | 100 | 100 | 100 | 100 |
| Use | Comb running | A | A | A | A | D | C |
| Effect | Flexibility | B | A | B | A | D | C |
| | Hair fixability | A | A | B | A | D | D |
| Feeling | Tackiness | A | A | B | A | D | D |
| of use | Finish | B | A | B | A | D | D |

Table 6

| Components | | Example (Specimen No.) | | |
|---|---|---|---|---|
| | | 33 | 34 | 35 |
| POP/POE cetyl ether (M.W. 3600) | | 10 | 10 | 10 |
| Liquid paraffin | | 10 | 10 | 10 |
| Silicone oil | | 0.5 | 0.5 | 0.5 |
| Oleyl oleate | | 1 | 3 | 5 |
| POE lauryl ether (HLB 13-16) | | 0.5 | 0.5 | 0.5 |
| POE cetyl ether (HLB 7-10) | | 1 | 1 | 1 |
| Distearyldimethylammonium chloride | | 1 | 1 | 1 |
| Stearic acid | | 2 | 2 | 2 |
| Cetyl alcohol | | 4 | 4 | 4 |
| Lanolin | | 3 | 3 | 3 |
| Propylene glycol | | 5 | 5 | 5 |
| Water | | 62 | 60 | 58 |
| | Total | 100 | 100 | 100 |
| use | Comb running | A | A | A |
| effect | Flexibility | A | A | A |
| | hair fixability | A | A | A |
| Feeling | Tackiness | A | A | A |
| of use | Finish | A | A | A |

As evident from the results shown in Tables 3 to 6, the hair conditioner compositions such as hair rinses, hair creams and hair treatment preparations according to this invention are all superior to the conventional products (Comparative Examples) in use effect such as comb running, flexibility and hair fixability as well as in feeling of use such as tackiness and performance. Also, any of the products of this invention could maintain a favorable emulsified condition and was also excellent in storage stability.

Although the present invention has been described with preferred embodiments, it is to be understood that variations and modifications may be resorted to as will be apparent to those skilled in the art. Such variations and modifications are to be considered within the purview and scope of the claims appended hereto.

What is claimed is:

1. A hair conditioner composition in the form of an oil-in-water type emulsion comprising 1 to 50% by weight of a high molecular synthetic oil with molecular weight over 1500 selected from the group consisting of polyalkylene glycol monoalkyl ethers, phosphates thereof and alkylene oxide polyol adducts 0.05 to 5% by weight of a cationic surface active agent, 0.5 to 10% by weight of a nonionic surface active agent and balance of water.

2. A hair conditioner composition as set forth in claim 1, further including 0.1 to 10% by weight of a liquid ester oil having good compatibility with said cationic surface active agent.

3. A hair conditioner composition as set forth in claim 1, wherein said non-ionic surface active agent and said cationic surface active agent are in the weight ratio of 5:1 to 1:5.

4. A hair conditioner composition as set forth in claim 2, wherein said non-ionic surface active agent and said cationic surface active agent are in the weight ratio of 5:1 to 1:5.

5. A hair conditioner composition as set forth in claim 1, wherein said non-ionic surface active agent is mainly composed of a combination of a polyoxyethylene alkyl ether with a hydrophilic-lipophilic balance of 7 to 10 and another polyoxyethylene alkyl ether with hydrophilic-lipophilic balance of 13 to 16 said ethers being in the weight ratio of 5:1 to 1:5.

6. A hair conditioner composition as set forth in claim 2, wherein said non-ionic surface active agent is mainly composed of a combination of a polyoxyethylene alkyl ether with hydrophilic-lipophilic balance of 7 to 10 and another polyoxyethylene alkyl ether with hydrophilic-lipophilic balance of 13 to 16 said ethers being in the weight ratio of 5:1 to 1:5.

* * * * *